US011845962B2

(12) United States Patent
Hong et al.

(10) Patent No.: US 11,845,962 B2
(45) Date of Patent: Dec. 19, 2023

(54) METHOD FOR LARGE-SCALE PRODUCTION OF LENTIVIRUS BY USING GMP-LEVEL SERUM-FREE SUSPENSION CELLS

(71) Applicant: SHANGHAI CELLULAR BIOPHARMACEUTICAL GROUP LTD., Shanghai (CN)

(72) Inventors: Yi Hong, Shanghai (CN); Ting Yan, Shanghai (CN); Jiangguo Ying, Shanghai (CN); Haojie Zhang, Shanghai (CN); Luyi Zhang, Shanghai (CN); Li Zhang, Shanghai (CN)

(73) Assignee: SHANGHAI CELLULAR BIOPHARMACEUTICAL GROUP LTD., Shanghai (CN)

( * ) Notice: Subject to any disclaimer, the term of this patent is extended or adjusted under 35 U.S.C. 154(b) by 743 days.

(21) Appl. No.: 17/041,578

(22) PCT Filed: Mar. 28, 2019

(86) PCT No.: PCT/CN2019/080215
§ 371 (c)(1),
(2) Date: Sep. 28, 2020

(87) PCT Pub. No.: WO2019/184996
PCT Pub. Date: Oct. 3, 2019

(65) Prior Publication Data
US 2021/0363497 A1 Nov. 25, 2021

(30) Foreign Application Priority Data
Mar. 29, 2018 (CN) .......................... 201810273392.7

(51) Int. Cl.
C12N 7/00 (2006.01)
C12N 15/86 (2006.01)

(52) U.S. Cl.
CPC .............. C12N 7/00 (2013.01); C12N 15/86 (2013.01); C12N 2740/15043 (2013.01); C12N 2740/15051 (2013.01); C12N 2740/16043 (2013.01); C12N 2740/16051 (2013.01)

(58) Field of Classification Search
None
See application file for complete search history.

(56) References Cited

U.S. PATENT DOCUMENTS

| | | |
|---|---|---|
| 2003/0175688 A1 | 9/2003 | Pennathur-Das et al. |
| 2007/0249019 A1 | 10/2007 | Kang et al. |
| 2008/0026448 A1 | 1/2008 | Lyderson et al. |
| 2009/0175906 A1 | 7/2009 | Kaylan et al. |
| 2011/0207202 A1 | 8/2011 | Luitjens et al. |
| 2014/0315294 A1 | 10/2014 | Marceau et al. |
| 2015/0133636 A1 | 5/2015 | Xenopoulos et al. |
| 2017/0002332 A1 | 1/2017 | Boudeffa et al. |
| 2021/0009966 A1 | 1/2021 | Hong et al. |
| 2021/0147826 A1 | 5/2021 | Hong et al. |

FOREIGN PATENT DOCUMENTS

| | | |
|---|---|---|
| CN | 103881984 A | 6/2014 |
| CN | 104371982 A | 2/2015 |
| CN | 106434571 A | 2/2017 |
| CN | 106474466 A | 3/2017 |
| CN | 107043784 A | 8/2017 |
| CN | 107384877 A | 11/2017 |
| CN | 107523555 A | 12/2017 |
| CN | 107523555 A | 12/2017 |
| CN | 107630037 A | 1/2018 |
| CN | 107841482 A | 3/2018 |
| JP | 2009-534030 A | 9/2009 |
| JP | 2017-503486 A | 2/2017 |
| JP | 2018-507707 A | 3/2018 |
| WO | 03/039459 A2 | 5/2003 |
| WO | 2013/076309 A1 | 5/2013 |
| WO | WO-2013/076309 A1 | 5/2013 |
| WO | 2016/128408 A | 5/2016 |

OTHER PUBLICATIONS

CN107523555A—The method for obtaining virus—Google Patents Machine Translation available Dec. 29, 2017.*
Ansorge, Sven, et al., "Recent progress in lentiviral vector mass production," Biochemical Engineering Journal, vol. 48, No. 3, Feb. 15, 2010, pp. 362-377.
Cai, Jingjing, et al., "Lentiviral Vector Packaging and Production Method," Journal of Yangtze University (Natural Science Edition), vol. 11, No. 9, Mar. 25, 2014, pp. 121-124.
International Search Report dated May 24, 2019 for PCT/2019/080215.
Broussau et al.: "Inducible Packaging Cells for Large-scale Production of Lentiviral Vectors in Serum-free Suspension Culture", Molecular Therapy, 2008, 16(3): 500-507.
Segura et al.: "Production of Lentiviral Vectors by Large-Scale Transient Transfection of Suspension Cultures and Affinity Chromatography Purification", Biotechnology and Bioengineering, 2007, 98(4): 789-799.
Witting et al: "Efficient Large Volume Lentiviral Vector Production Using Flow Electroporation", Human Gene Therapy, 2012, vol. 23, pp. 243-249.

(Continued)

Primary Examiner — Shanon A. Foley
(74) Attorney, Agent, or Firm — Leason Ellis LLP

(57) ABSTRACT

Provided is a method for large-scale production of lentivirus by using GMP-level serum-free suspension cells. Said method comprises the following steps: (a) providing a seed solution of packaged cells; (b) inoculating the seed solution in a first culture solution; (c) carrying out subculture of the packaged cells; (d) starting a liquid change operation when a liquid change trigger condition is met; (e) repeating steps (c) and (d) 1, 2 or 3 times; (f) starting a transfection operation when a transfection trigger condition is met; (g) optionally performing liquid change after transfection; (h) cultivating the transfected packaged cells; (i) starting harvesting and liquid change operations when a liquid change trigger condition is met; (j) repeating steps (h) and (i) 1, 2 or 3 times; (k) combining each of the recovered liquids; and (l) performing a purifying treatment. The culture solution used in each step is a serum-free cell culture solution.

10 Claims, No Drawings

(56) References Cited

OTHER PUBLICATIONS

Bandeira et al. Downstream Processing of Lentiviral Vectors: Releasing Bottlenecks, Human Gene Therapy Methods, 2012, vol. 23, No. 4, pp. 255-263.
International Search Report and Written Opinion in PCT/CN2019/080213, dated May 30, 2019.
Maria Mercedes Segura et al: "New developments in lentiviral vector design, production and purification", Expert Opinion on Biological Therapy, vol. 13, No. 7, 2013, pp. 987-101.
Ansorage S et al: "Development of a scalable process for high-yield lentiviral vector production by transient transfection of HEK293 suspension cultures", The Journal of Gene Medicine, vol. 11, No. 10, 2009, pp. 868-876.
Jiang et al., Purification of Rotavirus by using Multimode media Capto core 700, Chinese J. Biologicals, 2015, vol. 28 No. 1, pp. 72-78.
Cai et al.: Lentiviral Vector Packaging and Production Method, Journal of Yangtze University, Natural Science Edition, 2014, vol. 11, No. 9, pp. 121-123.
Ansorge et al. Recent progress in lentiviral vector mass production, Biochemical Engineering Journal, 2010, vol. 48, No. 3, pp. 362-374.
International Search Report and Written Opinion in PCT/CN2019/080215, dated May 24, 2019.

\* cited by examiner

METHOD FOR LARGE-SCALE PRODUCTION OF LENTIVIRUS BY USING GMP-LEVEL SERUM-FREE SUSPENSION CELLS

CROSS REFERENCES TO RELATED APPLICATIONS

This application is the National Stage of International Application No. PCT/CN2019/080215 filed Mar. 28, 2019, and claims benefit of Chinese Application No. 201810273392.7 filed on Mar. 29, 2018, both of which are herein incorporated by reference in their entirety.

TECHNICAL FIELD

The present invention relates to the field of biotechnology, and specifically to a method for large-scale production of lentivirus by using GMP-level serum-free suspension cells.

BACKGROUND

Gene therapy refers to the introduction of exogenous therapeutic genes into target cells to correct or compensate for diseases caused by gene defects and abnormalities, or refers to acting on the targets of diseases using products expressed by the exogenous genes to achieve the purpose of treatment.

One kind of commonly used recombinant lentivirus vector is gene therapy vector which is developed based on HIV-1 (human immunodeficiency virus type I). Different from general retroviral vectors, recombinant lentivirus vectors have the ability to infect both dividing cells and non-dividing cells. Recombinant lentivirus vectors have become preferred transgenic vectors for CART cells and gene therapy due to their high biological titer and low immunogenicity in vivo and in vitro. The mature HIV-1 virus has a diameter of 100-120 nm, a 20-hedron symmetrical structure, and a spherical shape. A dense coniform core can be observed under the electron microscope, and the virus contains viral RNA molecules and enzymes, and the latter comprise reverse transcriptase, integrase and protease. The outermost layer of HIV-1 is a lipoprotein envelope. There are two glycoproteins on the membrane: a surface protein (gp120) and an intrinsic protein (gp41), wherein gp120 is a spike protein and gp41 is a transmembrane protein. The inner surface of the envelope is a matrix composed of P17, and the inside of the envelope is RNA wrapped by capsid protein (P24).

As for the current recombinant lentiviral vectors, only the packaging signal and target gene transcription elements are left in the lentiviral genome using genetic modification methods, while the reverse transcriptase, envelope proteins VSVG, gag/pol, rev, tat and other structures or regulator genes are scattered on different vectors, and the disease genes are deleted at the same time to ensure the safety of the recombinant lentiviral vectors.

HEK293T is a cell line derived from human embryonic kidney epithelium. It is obtained from the HEK 293 cell line through adenovirus E1A gene transfection. It can express the large T antigen of SV40, and contains the SV40 replication origin and promoter region. The eukaryotic expression vectors containing the replication initiation site of SV40 virus can realize efficient replication and transcription in HEK 293T cells, thereby increasing the expression level of exogenous genes. Therefore, HEK293T cells are widely used in lentivirus packaging and can obtain lentivirus feed liquid with higher titer.

However, as a lentivirus production cell line, HEK293T cells still have the following defects: 1) the big T antigen has a potential carcinogenic risk, and if the downstream process cannot remove it well, there is a certain risk for clinical treatment, and the big T antigen has a certain degree of immunogenicity, which will increase the difficulty of clinical treatment; 2) HEK 293T is an adherent cell, which is difficult to be produced in a cell factory or spinner flasks to achieve industrialization; 3) the ability to stick to the wall is weak, therefore the cells are easy to fall off using microcarrier technology, and the toxin production efficiency is significantly reduced.

In addition, although some technologies have been developed to produce lentiviruses based on suspension cells, the existing production methods still have some deficiencies. For example, they are not suitable for large-scale production, and are difficult to meet the strict requirements of GMP production, and the resulting virus has a lower titer.

Therefore, there is an urgent need in the field to develop a method for large-scale and high-efficiency production of lentivirus through packaging cells under serum-free and suspension culture conditions.

SUMMARY OF THE INVENTION

The purpose of the present invention is to provide a method for large-scale and high-efficiency production of lentivirus through packaging cells under serum-free and suspension culture conditions.

In a first aspect of the present invention, it provides a method for producing lentivirus using serum-free suspension cells, which comprises the steps of:
- (a) providing a seed solution of packaging cells for the production of lentivirus, wherein the packaging cells are packaging cells that grow in suspension;
- (b) inoculating the seed solution in a first culture medium placed in a culture container to obtain a first culture, wherein the first culture medium is a serum-free cell culture medium, and the inoculation density is $1\times10^6$-$5\times10^6$ cells/ml, and the volume of the first culture medium is 3-100 liters (preferably 5-50 liters);
- (c) carrying out subculture of the packaging cells of the first culture, wherein the subculture conditions are set at a temperature of 30-38° C., a dissolved oxygen concentration of 35-55%, a $CO_2$ concentration of 2-10% and a pH of 6.9-7.4;
- (d) starting a liquid change operation when liquid change trigger conditions are met,
  wherein the liquid change trigger conditions comprise:
  - (s1) the real-time pH is ≤6.9, preferably ≤7.0, preferably ≤7.05;
  - (s2) the real-time pH value is still showing a downward trend by adjusting the concentration of oxygen, air, nitrogen and/or $CO_2$; and
  - (s3) the subculture time is ≥72 hours;
  wherein, the liquid change operation comprises: discharging the cell-free supernatant in the culture from the culture container, wherein the volume of the culture before discharging the supernatant is Vq1, while the volume of the culture after discharging the supernatant is Vh1, and the ratio of Vq1/Vh1 is 3-15 (preferably 4-7, more preferably 5-6); then, adding the culture medium to the culture container to form a packaging cell culture;

(e) repeating steps (c) and (d) n times, wherein n is 1, 2, or 3;

(f) starting a transfection operation when transfection trigger conditions are met, wherein, the transfection trigger conditions comprise:
(t1) the total number of cells is $0.05\text{-}2\times10^{11}$ cells;
(t2) the cell density is $0.5\text{-}5\times10^6$ cells/ml;
(t3) the cell viability rate is $\geq 90\%$; and
(t4) the total culture time is $\geq 72$ hours;

wherein, the transfection operation comprises: mixing a production plasmid used for producing the lentivirus with a transfection reagent, and adding the mixture to the culture container for introduction to the packaging cells to form transfected packaging cells;

(g) optionally carrying out post-transfection liquid change;

(h) culturing the transfected packaging cells, wherein the culture conditions are set at a temperature of 30-37° C., a dissolved oxygen concentration of 35-55%, a $CO_2$ concentration of 2-10% and a pH of 6.9-7.4;

(i) starting a harvest and liquid change operation when liquid change trigger conditions are met, wherein the liquid change trigger condition comprises:
(s1) the real-time pH is $\leq 6.9$, preferably$\leq 7.0$, preferably $\leq 7.05$;
(s2) the real-time pH value is still decreasing by adjusting the concentration of oxygen, air, nitrogen and/or $CO_2$; and
(s3) the subculture time is $\geq 72$ hours;

wherein the liquid change operation comprises: recovering the cell-free virus-containing feed liquid from the culture, wherein the volume of the culture before recovering the feed liquid is Vq2, while the volume of the culture after recovering of the supernatant is Vh2, and the ratio of Vq2/Vh2 is 3-15 (preferably 4-7, more preferably 5-6);

(j) repeating steps (h) and (i) m times, wherein m is 1, 2, or 3, and before repeating, adding culture medium to the culture container to form a transfected cell culture;

(k) mixing the recovered liquids from each recovery to obtain a mixed virus-containing supernatant; and (l) purifying the mixed virus-containing supernatant to obtain a purified lentiviral vector;

wherein, the culture medium used in all the above steps is a serum-free cell culture medium.

In another preferred embodiment, in step (d), the volume of the packaging cell culture is Vb1, and the ratio of Vb1:Vq1 is (0.8-1.2):1.

In another preferred embodiment, in step (j), the volume of the transfected cell culture is Vb2, and the ratio of Vb2:Vq2 is (0.8-1.2):1.

In another preferred embodiment, in step (c) and/or (h), the culture is performed under a shaking condition.

In another preferred embodiment, the shaking condition is a shaking speed of 10 to 30 rocks/min.

In another preferred embodiment, the amplitude of each rock is 1-20 cm, preferably 5-10 cm.

In another preferred embodiment, the culture medium added in different steps is the same or different culture mediums.

In another preferred embodiment, in step (c) and/or (h), the pH is maintained between 7.0 and 7.35.

In another preferred embodiment, in step (c) and/or (h), the dissolved oxygen concentration is maintained between 30% and 50%.

In another preferred embodiment, in step (c) and/or (h), the concentration of $CO_2$ is maintained between 3-5%.

In another preferred embodiment, in step (d) and/or (i), the ratio of Vq1/Vh1 is 5-10.

In another preferred embodiment, the total time of steps (c), (d), and (e) is 72-216 hours. (Before transfection)

In another preferred embodiment, the total time of steps (f), (g), (h), (i) and (j) is 72-120 hours. (After transfection)

In another preferred embodiment, in step (f), the multi-plasmid transfection comprises three-plasmid transfection and four-plasmid transfection.

In another preferred embodiment, the four-plasmid transfection is the transfection with plasmids CAR, gag/pol, rev, and VSVG.

In another preferred embodiment, the culture container is a disposable culture container.

In another preferred embodiment, the volume of the culture container is 20-120L, preferably 30-100L, more preferably 50-80L.

In another preferred embodiment, the total number of viruses contained in the mixed virus-containing supernatant is $1\times10^{12}$ Tu.

In another preferred embodiment, the virus titer of the mixed virus-containing supernatant is $8\times10^7$ Tu/ml.

In another preferred embodiment, the packaging cells are human embryonic kidney epithelial cells.

In another preferred embodiment, the packaging cells are human embryonic kidney epithelial cells HEK293F or derived cells thereof.

In another preferred embodiment, the serum-free medium is LV-MAX™ Production Medium (Gibco™)

In another preferred embodiment, in step (1), the purification comprises: ultrafiltration and chromatography.

It is to be understood that the various technical features of the present invention mentioned above and the various technical features specifically described hereinafter (as in the Examples) may be combined with each other within the scope of the present invention to constitute a new or preferred technical solution, which needs not be described one by one, due to space limitations.

DETAILED DESCRIPTION

After extensive and intensive research, through exploration of the production process and screening of process parameters, the inventors have for the first time developed a method for large-scale production of lentivirus by using GMP-level serum-free suspension cells. The method of the present invention is not only suitable for large-scale production of 50 liters or more, but also extremely efficient in preparing a high-titer lentivirus, and since the whole process adopts serum-free culture conditions, it avoids the risk of introduction of animal-based protein and other contaminants due to the use of serum. In addition, the volatility between batches of lentivirus produced by the method of the present invention is extremely small, so that the high requirements of GMP production for production quality can be met. The present invention has been completed on the basis of this.

Terms

As used herein, the terms "packaging cells of the present invention", "packaging cell HEK293F", "packaging cell HEK293F of the present invention" are used interchangeably and refer to the cells used for package and production of lentivirus described in the first aspect of the present invention.

Packaging Cells and Packaging System

In the present invention, the lentivirus packaging system that can be used is not particularly limited. Preferably, a three-plasmid and four-plasmid system can be used.

A particularly preferred packaging system is a lentiviral vector derived from HIV-1, wherein a four-plasmid system is used instead of a three-plasmid system. Besides, the tat regulatory gene is knocked out and the gag/pol and rev carrier plasmids are split into two, thereby reducing the possibility of the production of replicating viruses and greatly increasing the safety of the vector system.

In the preferred embodiment of the present invention, the lentivirus production is performed with four-plasmid system to further ensure the safety and reliability of the lentivirus product.

The main advantages of the present invention are as Follows.

(a) The cells of the present invention are suspension culture cells, and the process can be scaled up with an automatic control system, so that the recombinant lentiviral vector feed liquid can be produced on a large scale, and the production cost can be controlled.

(b) The cell culture process of the present invention adopts a one-time culture technology and uses a serum-free and protein-free medium, which avoids the risk of contamination by heterologous proteins and mad cow disease virus in the final product, and greatly improves the safety of clinical application of the product, thereby can be used in the production of cell or gene medicines.

The present invention will be further illustrated below with reference to the specific examples. It is to be understood that these examples are for illustrative purposes only and are not intended to limit the scope of the invention. For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified. Unless indicated otherwise, parts and percentage are weight parts and weight percentage.

General Methods and Materials

Medium: a serum-free, protein-free, and chemically defined medium.

Culture conditions: $CO_2$ concentration is 3%-5%; temperature is 30-37° C.

(1) preparation of transfection reagent:
a) 1×HBS (pH 7.4): 8.76 g of NaCl was dissolved in 900 ml of ultrapure water, added with 20 ml of 1M HEPES, and the pH was adjusted to 7.4, and the volume was made to 1 L, and stored at 4° C. after filtration (0.2 μm filter membrane) for later use.
b) 125 mg of PEI powder was dissolved in 50 ml 1×HBS (pH 7.4), filtered with 0.2 μm filter membrane, and stored at 4° C. for later use.

EXAMPLE 1

Method for Large-Scale Production of Lentivirus

The present method provided is a method for large-scale production of lentivirus by using GMP-level serum-free suspension cells.

The method of the present invention comprises the steps of:

(a) providing a seed solution of packaging cells for the production of lentivirus, wherein the packaging cells are packaging cells that grow in suspension;

(b) inoculating the seed solution in a first culture medium placed in a culture container to obtain a first culture, wherein the first culture medium is a serum-free cell culture medium, and the inoculation density is $1\times10^6$-$5\times10^6$ cells/ml, and the volume of the first culture medium is a predetermined volume (such as 3-100 liters);

(c) carrying out subculture of the packaging cells of the first culture, wherein the subculture conditions are set at a temperature of 30-38° C., a dissolved oxygen concentration of 35-55%, a $CO_2$ concentration of 2-10% and a pH of 6.9-7.4;

(d) starting a liquid change operation when the liquid change trigger conditions are met,
wherein, the liquid change operation comprises: discharging the cell-free supernatant in the culture from the culture container; then, adding the culture medium to the culture container to form a packaging cell culture;

(e) repeating steps (c) and (d) n times, n is 1, 2, or 3;

(f) starting a transfection operation when the transfection trigger conditions are met,
wherein, the transfection operation comprises: mixing a production plasmid used for producing the lentivirus with a transfection reagent, and adding the mixture to the culture container for introduction to the packaging cells to form transfected packaging cells;

(g) optionally carrying out post-transfection liquid change;

(h) culturing the transfected packaging cells, wherein the culture conditions are set at a temperature of 30-37° C., a dissolved oxygen concentration of 35-55%, a $CO_2$ concentration of 2-10% and a pH of 6.9-7.4;

(i) starting a harvest and liquid change operation when the liquid change trigger conditions are met,
wherein, the liquid change operation comprises: recovering the cell-free virus-containing feed liquid from the culture;

(j) repeating steps (h) and (i) m times, wherein m is 1, 2, or 3, and before repeating, adding culture medium to the culture container to form a transfected cell culture;

(k) mixing the recovered liquids from each recovery to obtain a mixed virus-containing supernatant; and (l) purifying the mixed virus-containing supernatant to obtain a purified lentiviral vector;
wherein, the culture medium used in all the above steps is a serum-free cell culture medium.

In the present invention, the liquid change trigger conditions have been optimized, which helps to reduce the quality fluctuation of each production batch and helps to obtain high-titer and high-yield medical-grade lentivirus. Typically, the liquid change trigger conditions comprise:

(s1) the real-time pH is ≤6.9, preferably ≤7.0, preferably ≤7.05;

(s2) the real-time pH value is still showing a downward trend by adjusting the concentration of oxygen, air, nitrogen and/or $CO_2$; and (s3) the subculture time is ≥72 hours;

In the present invention, the transfection trigger conditions have been optimized, which helps to reduce the quality fluctuation of each production batch and helps to obtain high-titer and high-yield medical-grade lentivirus. Typically, the transfection trigger conditions comprise:

(t1) the total number of cells is $0.05$-$2\times10^{11}$ cells;

(t2) the cell density is $0.5$-$5\times10^6$ cells/ml;

(t3) the cell viability rate is ≥90%; and (t4) the total culture time is ≥72 hours;

Typically, in a specific embodiment of the present invention, the method comprises the steps of: preparation of seed solution;

inoculating (inoculated in a 25L culture medium) at an inoculation density of $1-5\times10^6$ cells/ml;

carrying out a subculture of the packaging cells (through the adjusting of pH and dissolved oxygen concentration, automatically adjusting the aeration ratio of dissolved $CO_2$, nitrogen, and air during the culture, and the start mode of liquid change), controlling the pH at 6.9-7.4, preferably 7.0-7.3, more preferably 7.1-7.2;

preforming the first liquid change (when pH≤6.9, preferably ≤7.0, the liquid change can be triggered), for example 25L→2-10L (preferably 3-7L);

adding serum-free culture medium and continuing the culture for 24-96 hours, preferably 36-72 hours, more preferably 40-60 hours; and when cultured for 300 hours, the number of cells was $5\times10^{10}$;

adding plasmids to preform multi-plasmid transfection on the packaging cells;

optional step: after transfection, incubating for 2-10 hours, preferably 4-6 hours, and changing the liquid again (first discharging a certain amount of culture mixture, and then adding serum-free culture medium);

general step: after transfection, continuing the culture, triggering the first liquid change after transfection when pH≤6.9, preferably ≤7.0, recovering the discharged liquid culture mixture (cell-free virus-containing supernatant) and denoting it as recovery solution R1, and storing at 2-8° C.;

after liquid change, continuing the culture, and when the liquid change conditions are triggered, performing the i-th liquid change after transfection, wherein i is 2, 3, 4 and 5; recovering the cell-free virus-containing supernatant in the discharged liquid culture mixture during each liquid change and denoting it as the recovery solution Ri, wherein this step is repeated 1, 2 or 3 times;

mixing the recovered liquids from each recovery to obtain a mixed virus-containing supernatant;

purifying the mixed virus-containing supernatant to obtain a purified lentiviral vector, whose titer is $1\times10^8-1\times10^9$Tu/mL.

COMPARATIVE EXAMPLE 1

Example 1 was repeated, wherein the difference is: the initial pH is 6.9-7.4, but the real-time pH value of the first culture is not monitored in real time during the subculture, and the subculture is carried out 24 to 96 hours thereafter.

Results: when cultured to 300 h, the number of cells was $4\times10^9$ (less than the preferred example).

COMPARATIVE EXAMPLE 2

Example 1 was repeated, wherein the difference is: $CO_2$ content is not adjusted.

Results: the biological titer of lentivirus was 20% of that in the preferred example.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. A method for producing lentivirus using serum-free suspension cells, which comprises the steps of:

(a) providing a seed solution of packaging cells for the production of lentivirus, wherein the packaging cells are packaging cells that grow in suspension;

(b) inoculating the seed solution in a first culture medium placed in a culture container to obtain a first culture, wherein the first culture medium is a serum-free cell culture medium, and the inoculation density is $1\times10^6$-$5\times10^6$cells/ml, and the volume of the first culture medium is 3-100 liters;

(c) carrying out subculture of the packaging cells of the first culture, wherein the subculture conditions are set at a temperature of 30-38° C., a dissolved oxygen concentration of 35-55%, a $CO_2$ concentration of 2-10% and a pH of 6.9-7.4, and monitoring the real-time pH value of the first culture during the subculture process, and controlling dissolved oxygen and/or $CO_2$ concentrations based on the real-time pH value to maintain the pH between 6.9-7.4;

(d) starting a liquid change operation when liquid change trigger conditions are met, wherein the liquid change trigger conditions comprise:
(s1) the real-time pH is ≤6.9 or ≤7.0 or ≤7.05;
(s2) the real-time pH value is still showing a downward trend by adjusting the concentration of oxygen, air, nitrogen and/or $CO_2$; and
(s3) the subculture time is ≥72 hours;

wherein, the liquid change operation comprises: discharging the cell-free supernatant in the culture from the culture container, wherein the volume of the culture before discharging the supernatant is Vq1, while the volume of the culture after discharging the supernatant is Vh1, and the ratio of Vq1/Vh1 is 3-15; then, adding the culture medium to the culture container to form a packaging cell culture;

(e) repeating steps (c) and (d) n times, wherein n is 1, 2, or 3;

(f) starting a transfection operation when transfection trigger conditions are met, wherein, the transfection trigger conditions comprise:
(t1) the total number of cells is $0.05-2\times10^{11}$ cells;
(t2) the cell density is $0.5-5\times10^6$ cells/ml;
(t3) the cell viability rate is ≥90%; and
(t4) the total culture time is ≥72 hours;

wherein, the transfection operation comprises: mixing a production plasmid used for producing the lentivirus with a transfection reagent, and adding the mixture to the culture container for introduction to the packaging cells to form transfected packaging cells;

(g) optionally carrying out post-transfection liquid change;

(h) culturing the transfected packaging cells, wherein the culture conditions are set at a temperature of 30-37° C., a dissolved oxygen concentration of 35-55%, a $CO_2$ concentration of 2-10% and a pH of 6.9-7.4, and monitoring the real-time pH value of the first culture during the subculture process, and controlling dissolved oxygen and/or $CO_2$ concentrations based on the real-time pH value to maintain the pH between 6.9-7.4;

(i) starting a harvest and liquid change operation when liquid change trigger conditions are met, wherein the liquid change trigger conditions comprise:
(s1) the real-time pH is ≤6.9;
(s2) the real-time pH value is still decreasing by adjusting the concentration of oxygen, air, nitrogen and/or $CO_2$; and
(s3) the subculture time is ≥72 hours;

wherein the liquid change operation comprises: recovering the cell-free virus-containing feed liquid from the culture, wherein the volume of the culture before recovering the feed liquid is Vq2, while the volume of the culture after recovering of the supernatant is Vh2, and the ratio of Vq2/Vh2 is 3-15;

(j) repeating steps (h) and (i) m times, wherein m is 1, 2, or 3, and before repeating, adding culture medium to the culture container to form a transfected cell culture;

(k) mixing the recovered liquids from each recovery to obtain a combined virus-containing supernatant; and (l) purifying the mixed virus-containing supernatant to obtain a purified lentiviral vector;

wherein, the culture medium used in all the above steps is a serum-free cell culture medium.

2. The method of claim 1, wherein in step (c) and/or (h), the culture is performed under a shaking condition.

3. The method of claim 1, wherein in step (c) and/or (h), the pH is maintained between 7.0 and 7.35.

4. The method of claim 1, wherein in step (d) and/or (i), the ratio of Vq1/Vh1 is 5-10.

5. The method of claim 1, wherein the total time of steps (c), (d) and (e) is 72-216 hours.

6. The method of claim 1, wherein in step (f), the multi-plasmid transfection comprises three-plasmid transfection and four-plasmid transfection.

7. The method of claim 1, wherein the culture container is a disposable culture container.

8. The method of claim 1, wherein the total number of viruses contained in the mixed virus-containing supernatant is $1\times10^{12}$ Tu.

9. The method of claim 1, wherein the packaging cells are human embryonic kidney epithelial cells.

10. The method of claim 1, wherein in step (1), the purification comprises: ultrafiltration and chromatography.

* * * * *